United States Patent [19]
Fateley

[11] Patent Number: 6,128,078
[45] Date of Patent: *Oct. 3, 2000

[54] RADIATION FILTER, SPECTROMETER AND IMAGER USING A MICRO-MIRROR ARRAY

[75] Inventor: William G. Fateley, Manhattan, Kans.

[73] Assignee: Three LC, Inc., Manhattan, Kans.

[*] Notice: This patent is subject to a terminal disclaimer.

[21] Appl. No.: 09/502,758

[22] Filed: Feb. 11, 2000

Related U.S. Application Data

[63] Continuation of application No. 09/289,482, Apr. 9, 1999, Pat. No. 6,046,808.

[51] Int. Cl.[7] .................................. G01J 3/02; G01J 3/18
[52] U.S. Cl. ............................................. 356/330; 356/328
[58] Field of Search .................................... 356/310, 326, 356/328, 330

[56] References Cited

U.S. PATENT DOCUMENTS

| | | | |
|---|---|---|---|
| 4,193,691 | 3/1980 | Fjarlie | 356/330 |
| 4,790,654 | 12/1988 | Clarke | 356/310 |
| 5,061,049 | 10/1991 | Hornbeck | 359/224 |
| 5,323,002 | 6/1994 | Sampsell et al. | 250/252.1 |
| 5,504,575 | 4/1996 | Stafford | 356/330 |
| 5,506,676 | 4/1996 | Hendler et al. | 356/73 |
| 5,737,075 | 4/1998 | Koch et al. | 356/310 |
| 5,748,308 | 5/1998 | Lindberg et al. | 356/310 |
| 5,828,066 | 10/1998 | Messerschmidt | 250/339.07 |
| 6,046,808 | 4/2000 | Fateley | 356/330 |

*Primary Examiner*—F. L. Evans
*Attorney, Agent, or Firm*—Hovey, Williams, Timmons & Collins

[57] ABSTRACT

A spectrometer (10) includes a two-dimensional array of modulatable micro-mirrors (18), a detector (20), and an analyzer (22). The array of micro-mirrors is positioned for receiving individual radiation components forming a part of an input radiation source. The micro-mirrors are modulated at different modulation rates in order to reflect individual radiation components therefrom at known and different modulation rates. The micro-mirror array combines a number of the reflected individual radiation components and reflects the combined components to the detector. The detector is oriented to receive the combined radiation components reflected from the array and is operable to create an output signal representative thereof. The analyzer is operably coupled with the detector to receive the output signal and to analyze at least some of the individual radiation components making up the combined reflection. By using a micro-mirror that receives individual radiation components and then modulates the radiation components at different rates, all of the radiation components can be focused onto a single detector to maximize the signal-to-noise ratio of the detector. A variable band pass filter spectrometer, variable band reject filter spectrometer, variable multiple band pass filter spectrometer, and a variable multiple band reject filter spectrometer utilizing the same invention are also disclosed.

18 Claims, 5 Drawing Sheets

RADIATION FILTER, SPECTROMETER AND IMAGER USING A MICRO-MIRROR ARRAY

RELATED APPLICATION

This is a continuation application of Ser. No. 09/289,482 filed Apr. 9, 1999, now U.S. Pat. No. 6,046,808.

BACKGROUND OF THE INVENTION

1. Field of the Invention

The present invention relates to imagers, spectrometers, variable band pass filters or variable multiple band pass filters that include a micro-mirror array having a plurality of micro-mirrors that each can be individually modulated at a different modulation rate.

2. Description of the Prior Art

Imagers employ either a two-dimensional (2D) multi-channel detector array or a single element detector. Imagers using a 2D detector array measure the intensity distribution of all spatial resolution elements simultaneously during the entire period of data acquisition. Imagers using a single detector require that the individual spatial resolution elements be measured consecutively via a raster scan so that each one is observed for a small fraction of the period of data acquisition. Prior art imagers using a plurality of detectors at the image plane can exhibit serious signal-to-noise ratio problems. Prior art imagers using a single element detector can exhibit more serious signal-to-noise ratio problems. Signal-to-noise ratio problems limit the utility of imagers applied to chemical imaging applications where subtle differences between a sample's constituents become important.

Spectrometers are commonly used to analyze the chemical composition of samples by determining the absorption or attenuation of certain wavelengths of electromagnetic radiation by the sample or samples. Because it is typically necessary to analyze the absorption characteristics of more than one wavelength of radiation to identify a compound, and because each wavelength must be separately detected to distinguish the wavelengths, prior art spectrometers utilize a plurality of detectors, have a moving grating, or use a set of filter elements. However, the use of a plurality of detectors or the use of a macro moving grating has signal-to-noise limitations. The signal-to-noise ratio largely dictates the ability of the spectrometer to analyze with accuracy all of the constituents of a sample, especially when some of the constituents of the sample account for an extremely small proportion of the sample. There is, therefore, a need for imagers and spectrometers with improved signal-to-noise ratios.

Prior art variable band pass filter spectrometers, variable band reject filter spectrometers, variable multiple band pass filter spectrometers or variable multiple band reject filter spectrometers typically employ a multitude of filters that require macro moving parts or other physical manipulation in order to switch between individual filter elements or sets of filter elements for each measurement. Each filter element employed can be very expensive, difficult to manufacture and all are permanently set at the time of manufacture in the wavelengths (bands) of radiation that they pass or reject. Physical human handling of the filter elements can damage them and it is time consuming to change filter elements. There is, therefore, a need for variable band pass filter spectrometers, variable band reject filter spectrometers, variable multiple band pass filter spectrometers or variable multiple band reject filter spectrometers without a requirement for discrete (individual) filter elements that have permanently set band pass or band reject properties. There is also a need for variable band pass filter spectrometers, variable band reject filter spectrometers, variable multiple band pass filter spectrometers or variable multiple band reject filter spectrometers to be able to change the filters corresponding to the bands of radiation that are passed or rejected rapidly, without macro moving parts and without human interaction.

OBJECTS AND SUMMARY OF THE INVENTION

The present invention solves the above-described problems and provides a distinct advance in the art by providing an imager or spectrometer that is much less sensitive to ambient noise and that can effectively operate even when used in environments with a high level of ambient radiation. The invention further advances the art of variable band pass filter spectrometers, variable band reject filter spectrometers, variable multiple band pass filter spectrometers or variable multiple band reject filter spectrometers by providing a variable band pass filter spectrometer, variable band reject filter spectrometer, variable multiple band pass filter spectrometer or variable multiple band reject filter spectrometer that:

(1) does not require the selection of the bands of wavelengths passed or rejected at the time of manufacture;

(2) allows the selection of any desired combination of bands of wavelengths that are passed or rejected;

(3) reduces the time to change the bands of wavelengths passed or rejected; and (4) requires no macro moving parts to accomplish a change in the bands of wavelengths passed or rejected.

The present invention broadly includes a two-dimensional array of modulateable micro-mirrors, a detector, and an analyzer. The array of micro-mirrors is positioned for receiving an image. The micro-mirrors are modulated at known and selectively different modulation rates in order to reflect individual spatially distributed radiation components of the image therefrom at known and different modulation rates toward the detector.

The detector is oriented to receive the combined radiation components reflected from the array and is operable to generate an output signal representative of the combined radiation incident thereon. The analyzer is operably coupled with the detector to receive the output signal and to demodulate the signal to recover signals representative of each of the individual spatially distributed radiation components of the image. The analyzer can be configured to recover all reflected components or to reject some unnecessary components of the recovered signals from the combined reflections.

By using a micro-mirror that receives the individual spectral or spatial radiation components and then modulates the radiation components at different modulation rates, all of the radiation components can be focused onto a single detector and then later demodulated to maximize the signal-to-noise ratio of the detector.

BRIEF DESCRIPTION OF THE DRAWING FIGURES

A preferred embodiment of the present invention is described in detail below with reference to the attached drawing figures, wherein.

DETAILED DESCRIPTION OF THE PREFERRED EMBODIMENTS

Figure 1:
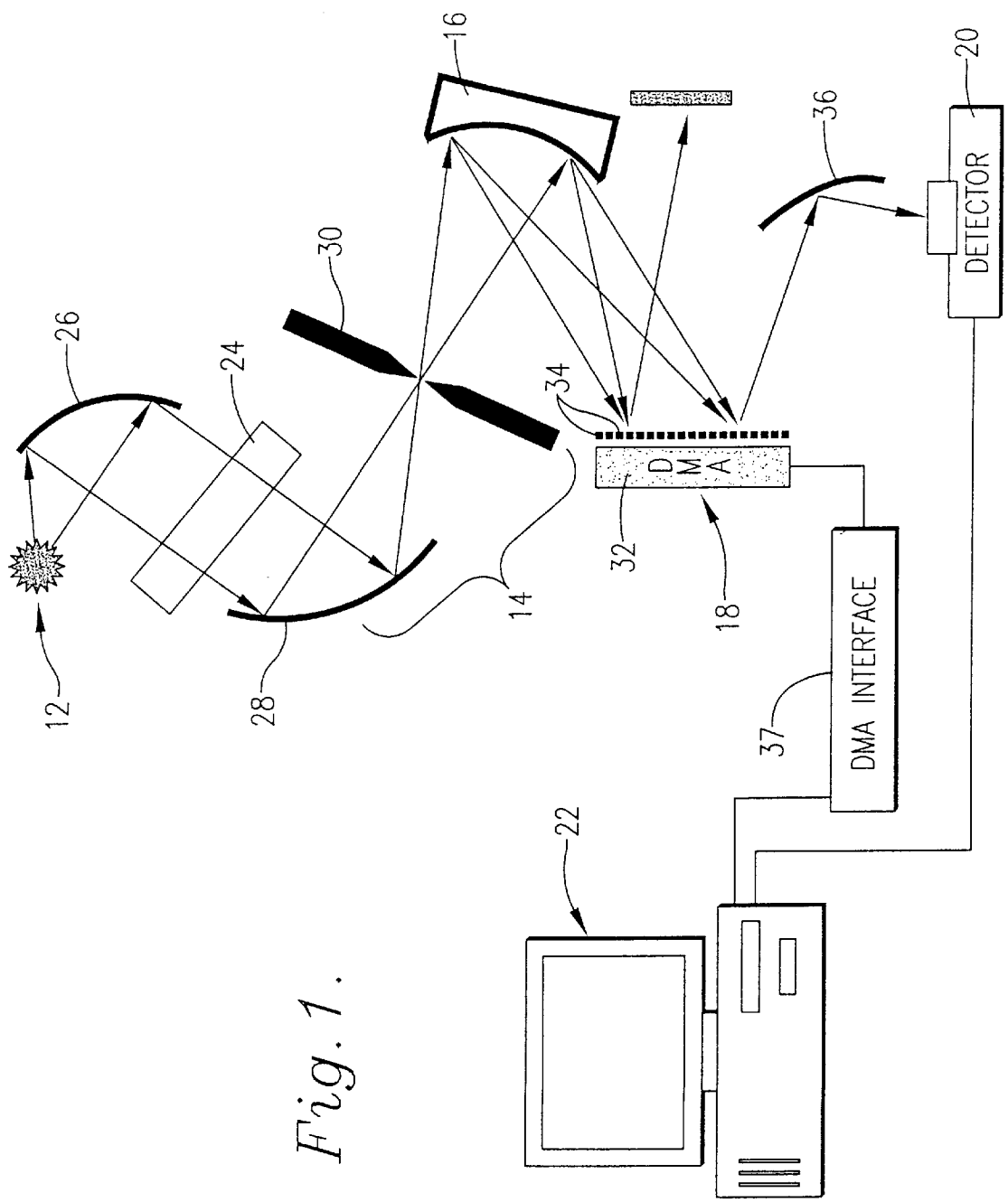
FIG. 1 is a schematic diagram illustrating a spectrometer constructed in accordance with one embodiment of the invention.

Turning now to the drawing figures and particularly FIG. 1, a spectrometer assembly 10 constructed in accordance with one embodiment of the invention is illustrated. The spectrometer broadly includes a source 12 of electromagnetic radiation, a mirror and slit assembly 14, a wavelength dispersing device 16, a spatial light modulator 18, a detector 20, and an analyzing device 22.

In more detail, the electromagnetic radiation source 12 is operable to project rays of radiation onto or through a sample 24 such as a sample of body tissue or blood. The radiation source may be any device that generates electromagnetic radiation in a known wavelength spectrum such as a globar, hot wire, or light bulb that produces radiation in the infrared spectrum. To increase the amount of rays that are directed to the sample, a parabolic reflector 26 may be interposed between the source 12 and the sample 24.

The mirror and slit assembly 14 is positioned to receive the radiation rays from the source 12 after they have passed through the sample 24 and is operable to focus the radiation onto and through the entrance slit 30. The collection mirror 28 focuses the radiation rays through slit 30 and illuminates the wavelength dispersing device 16.

The wavelength dispersing device 16 receives the beams of radiation from the mirror and slit assembly 14 and disperses the radiation into a series of lines of radiation each corresponding to a particular wavelength of the radiation spectrum. The preferred wavelength dispersing device is a concave diffraction grating; however, other wavelength dispersing devices such as a prism may be utilized.

Figure 2:
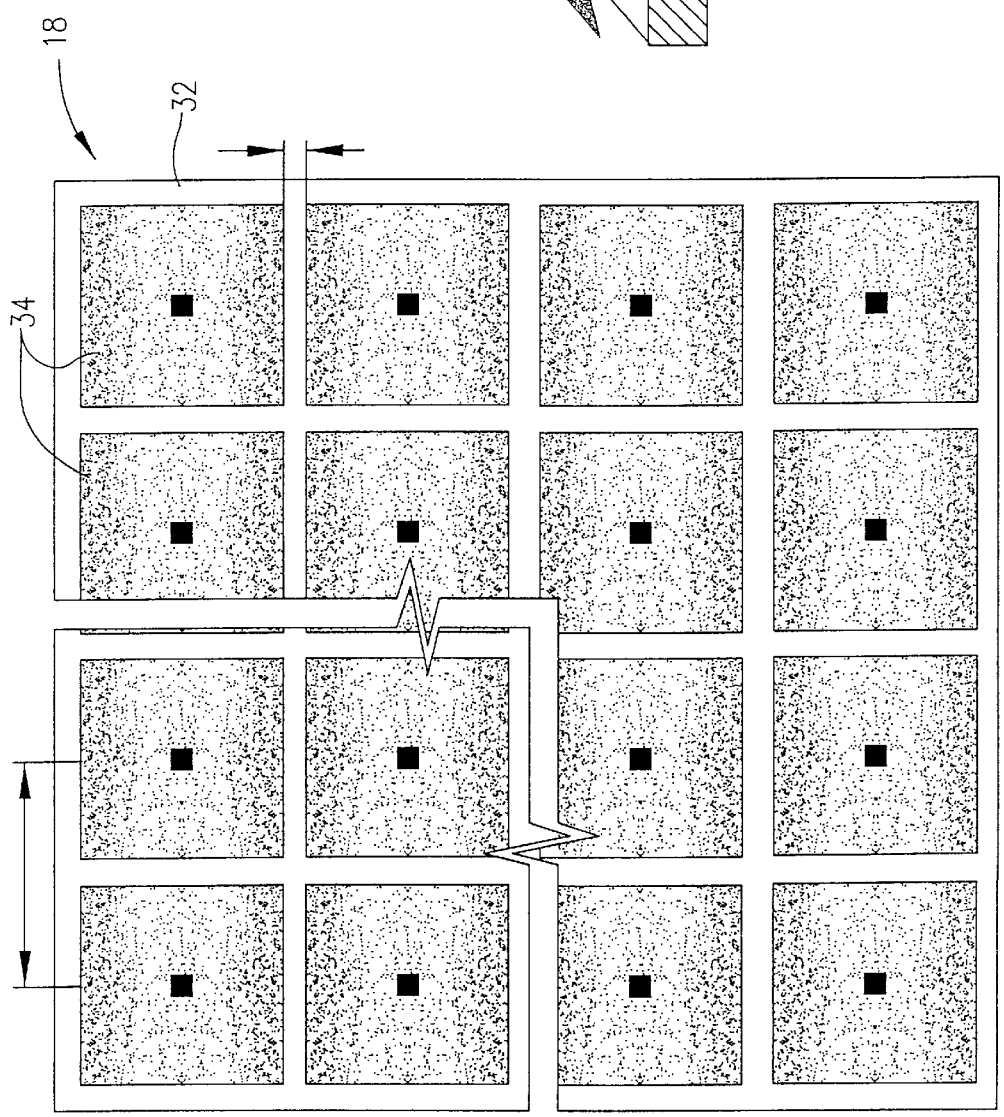
FIG. 2 is a plan view of a micro-mirror array used in the present invention.

The spatial light modulator 18 receives radiation from the wavelength dispersing device 16, individually modulates each spectral line, and reflects the modulated lines of radiation onto the detector 20. As best illustrated in FIG. 2, the spatial light modulator is preferably a micro-mirror array that includes a semi-conductor chip or piezio electric device 32 having an array of small reflecting surfaces 34 thereon that act as mirrors. One such micro-mirror array is manufactured by Texas Instruments and is described in more detail in U.S. Pat. No. 5,061,049, hereby incorporated into the present application by reference. Those skilled in the art will appreciate that other spatial light modulators such as a magneto optic modulator or a liquid crystal device may be used instead of the micro-mirror array.

Figure 3:
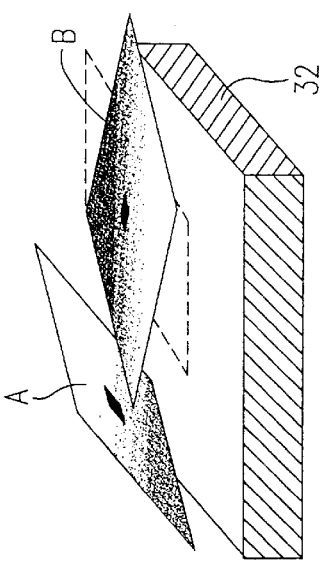
FIG. 3 is a schematic diagram of two micro-mirrors illustrating the modulations of the mirrors of the micro-mirror device of FIG. 2.

The semi-conductor 32 of the micro-mirror array 18 is operable to individually tilt each mirror along its diagonal between a first position depicted by the letter A and a second position depicted by the letter B in FIG. 3. In preferred forms, the semi-conductor tilts each mirror 10 degrees in each direction from the horizontal. The tilting of the mirrors 34 is preferably controlled by the analyzing device 22, which may communicate with the micro-mirror array 18 through an interface 37.

The micro-mirror array 18 is positioned so that the wavelength dispersing device 16 reflects each of the lines of radiation upon a separate column or row of the array. Each column or row of mirrors is then tilted or wobbled at a specific and separate modulation frequency. For example, the first row of mirrors may be wobbled at a modulation frequency of 100 Hz, the second row at 200 Hz, the third row at 300 Hz, etc.

The mirrors are calibrated and positioned so that they reflect all of the modulated lines of radiation onto the detector 20. Thus, even though each column or row of mirrors modulates its corresponding line of radiation at a different modulation frequency, all of the lines of radiation are focused onto a single detector.

The detector 20, which may be any conventional radiation transducer or similar device, is oriented to receive the combined modulated lines of radiation from the micro-mirror array 18. The detector is operable for converting the radiation signals into a digital output signal that is representative of the combined radiation lines that are reflected from the micro-mirror array. A reflector 36 may be interposed between the as micro-mirror array 18 and the detector 20 to receive the combined modulated lines of radiation from the array and to focus the reflected lines onto the detector.

The analyzing device 22 is operably coupled with the detector 20 and is operable to receive and analyze the digital output signal from the detector. The analyzing device uses digital processing techniques to demodulate the signal into separate signals each representative of a separate line of radiation reflected from the micro-mirror array. For example, the analyzing device may use discrete Fourier transform processing to demodulate the signal to determine, in real time, the intensity of each line of radiation reflected onto the detector. Thus, even though all of the lines of radiation from the micro-mirror array are focused onto a single detector, the analyzing device can separately analyze the characteristics of each line of radiation for use in analyzing the composition of the sample.

Figure 4:
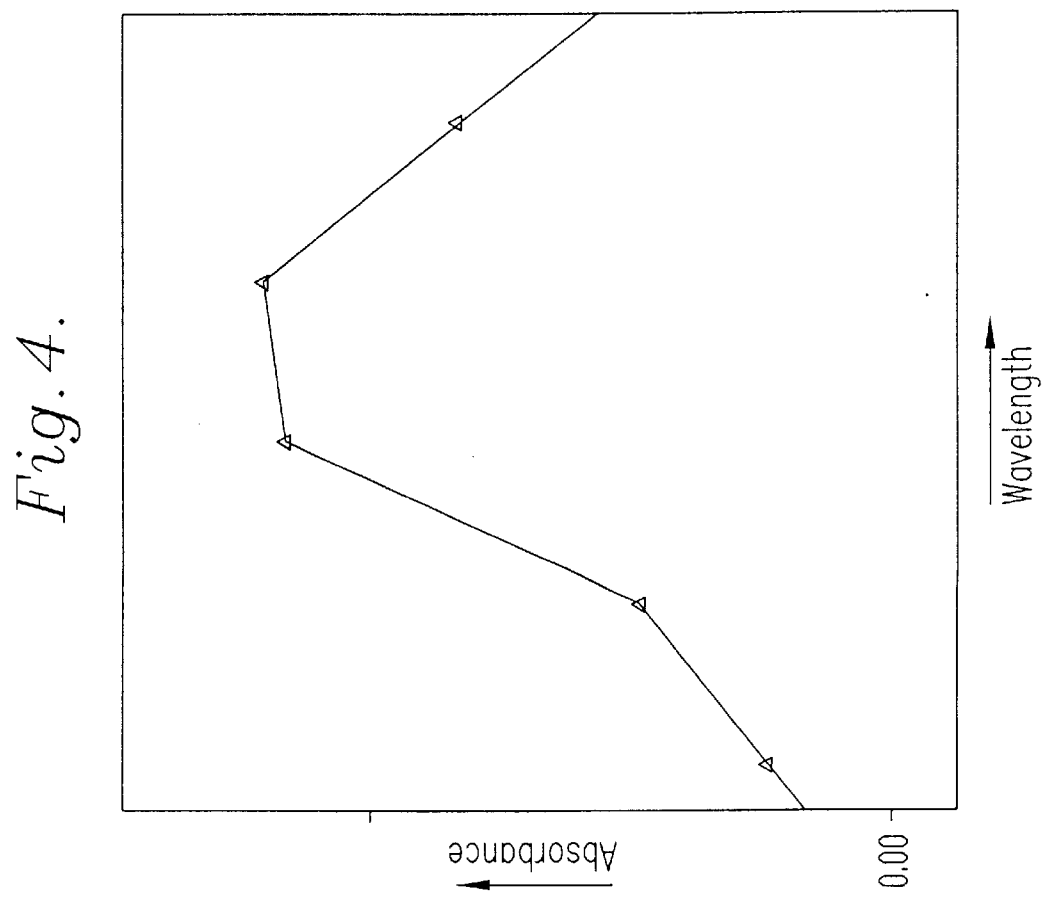
FIG. 4 is a graph illustrating an output signal of the spectrometer when used to analyze the composition of a sample.

The analyzing device is preferably a computer that includes spectral analysis software. FIG. 4 illustrates an output signal generated by the analyzing device. The output signal is a plot of the absorption characteristics of five wavelengths of radiation from a radiation source that has passed through a sample.

Figure 5:
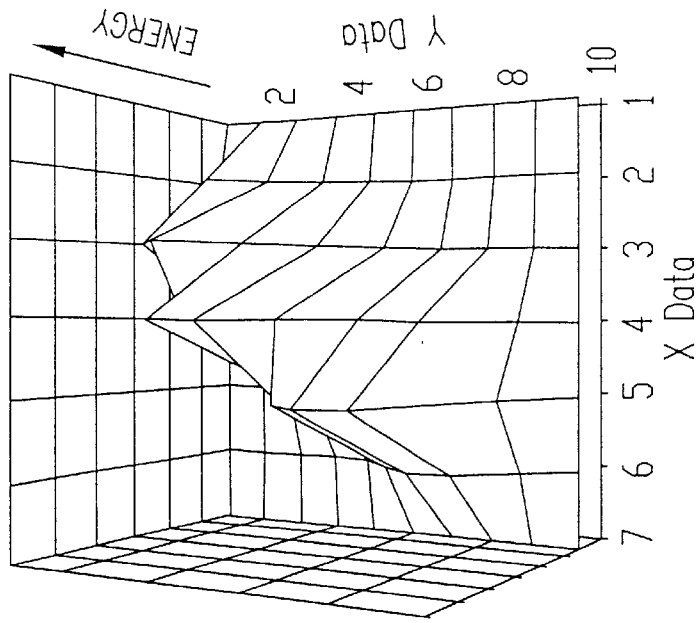
FIG. 5 is a graph illustrating an output signal of the imager when used for imaging purposes.
Figure 6:
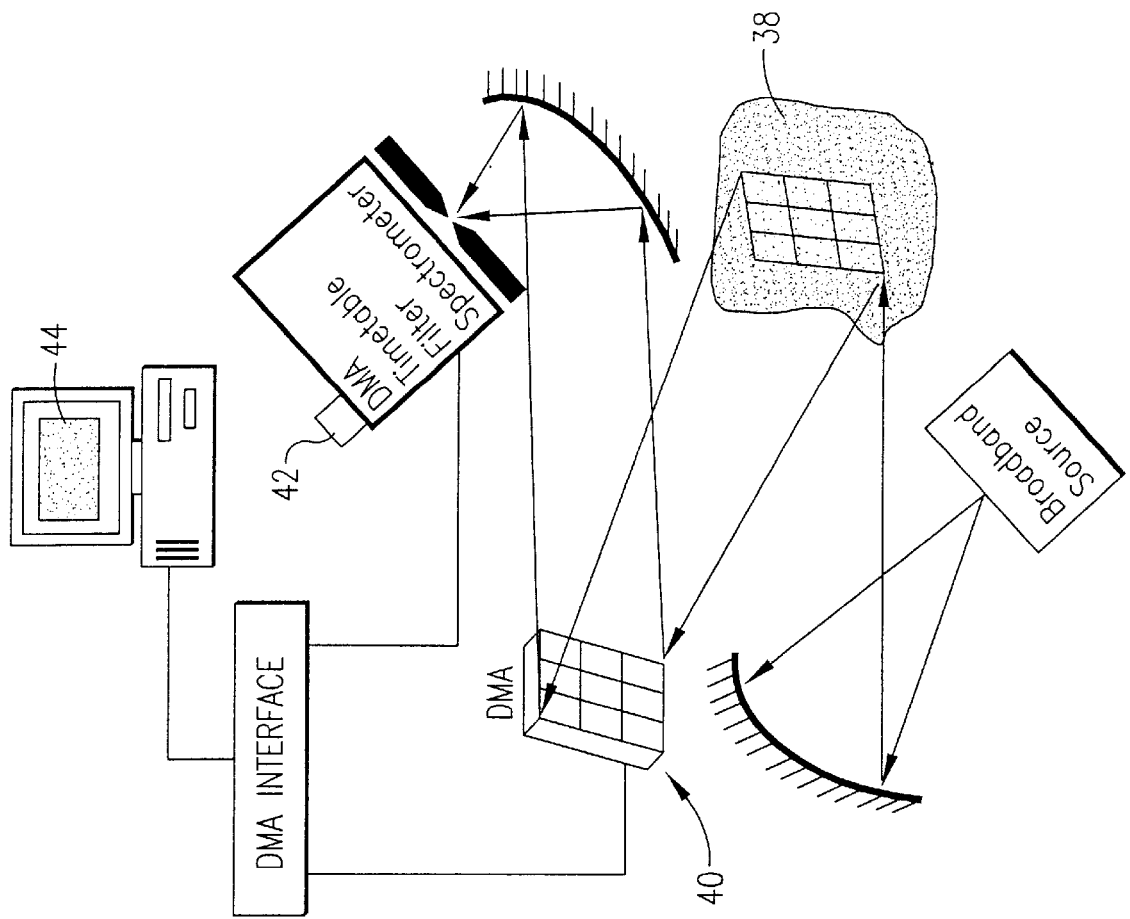
FIG. 6 is a schematic diagram illustrating an imager constructed in accordance with a preferred embodiment of the invention.

In a preferred embodiment of the invention illustrated in FIG. 6, the invention is used for digital imaging purposes. As an imaging device, an image of a sample 38 is focused onto a micro-mirror array 40 and each micro-mirror in the array is modulated at a different modulation rate. The micro-mirror array geometry is such that some or all of the reflected radiation impinges upon a single detector element 42 and is subsequently demodulated to reconstruct the original image improving the signal-to-noise ratio of the imager. Specifically, an analyzing device 44 digitally processes the combined signal to analyze the magnitude of each individual pixel. FIG. 5 is a plot of a three dimensional image showing the magnitude of each individual pixel.

Figure 7:
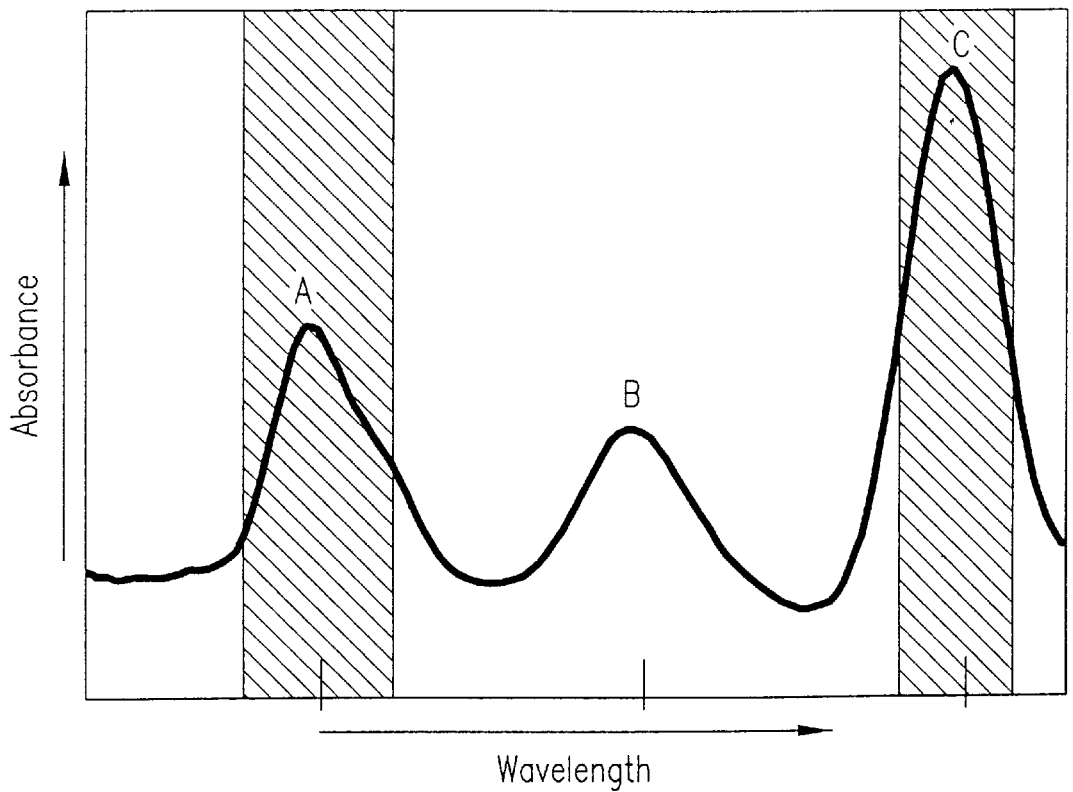
FIG. 7 is an illustration of the input to the DMA Filter Spectrometer and its use to pass or reject wavelength of radiation specific to constituents in a sample.

FIG. 7 illustrates the output of a digital micro-mirror array (DMA) filter spectrometer used as a variable band pass filter spectrometer, variable band reject filter spectrometer, variable multiple band pass filter spectrometer or variable multiple band reject filter spectrometer. In this example the combined measurement of the electromagnetic energy absorbed by sample constituents A and C is of interest. The shaded regions in FIG. 7 illustrate the different regions of the electromagnetic spectrum that will be allowed to pass to the detector by the DMA filter spectrometer. The wavelengths of electromagnetic radiation selected to pass to the detector correspond to the absorption band for compound A and absorption band for compound C in a sample consisting of compounds A, B, and C. The spectral region corresponding to the absorption band of compound B and all other wavelengths of electromagnetic radiation are rejected. Those skilled in the art will appreciate that the DMA filter spectrometer is not limited to the above example and can be used to pass or reject any combination of spectral resolution elements available to the DMA.

As a DMA filter imager the spatial resolution elements (pixels) of an image can be selectively passed or rejected (filtered) according to the requirements of the image measurement. The advantages of both the DMA filter spectrometer and DMA filter imager are:

(1) All spectral resolution elements or spatial resolution elements corresponding to the compounds of interest in a particular sample can be directed simultaneously to the detector for measurement. This has the effect of increasing the signal-to-noise ratio of the measurement.

(2) The amount of data requiring processing is reduced. This reduces storage requirements and processing times.

Although the invention has been described with reference to the preferred embodiment illustrated in the attached drawing figures, it is noted that equivalents may be employed and substitutions made herein without departing from the scope of the invention as recited in the claims. For example, although the imager and spectrometer are particularly useful for spectral analysis in the infrared spectrum, they can be used for analysis in any wavelength spectrum.

It can be noted that in FIG. 6 the sample is illuminated with broadband radiation and the image of the broadly illuminated sample is focused onto the DMA for encoding before being passed to a detector or DMA tunable filter spectrometer. This configuration we will call post-sample encoding. In another configuration we will call pre-sample encoding the broadband source illuminates the DMA and the modulations of the micro-mirrors in the DMA encode the source radiation prior to impinging upon the sample. The reflected radiation is then collected from the sample and directed onto the detector of into the DMA tunable filter spectrometer for spectral characterization.

Having thus described the preferred embodiment of the invention, what is claimed as new and desired to be protected by letters patent includes the following:

I claim:

1. An analysis assembly for analyzing the absorption or attenuation by a sample of input radiation having a plurality of individual radiation components, said assembly comprising:
    a plurality of modulatable micro-mirrors located for receiving individual radiation components forming a part of said input radiation, said micro-mirrors being modulatable at different modulation rates in order to reflect individual radiation components therefrom at known and different modulation rates and for combining a number of the reflected individual radiation components to generate a combined reflection;
    a detector oriented to receive said combined reflection from said micro-mirrors, and operable to create an output signal representative of said combined number of individual radiation components; and
    an analyzer operably coupled with said detector to receive said output signal, and providing an individual analyses of at least some of said individual radiation components making up said combined reflection.

2. The assembly of claim 1, said analyzer comprising a computer operably coupled with said detector and said micro-mirrors for controlling the modulation of said micro-mirrors and for providing said individual analyses.

3. The assembly of claim 1, further including a reflector positioned between the detector and the micro-mirrors and operable to receive said combined reflection from said micro-mirrors and to focus the combined reflection on said detector.

4. The assembly of claim 1, said analyzer operable to perform a Fourier analysis upon said output.

5. The assembly of claim 1, said individual analyses comprising the energy magnitude of said individual radiation components.

6. The assembly of claim 1, said input radiation being electromagnetic radiation.

7. The assembly of claim 1, said individual radiation components comprising different, substantially constant wavelength radiation components.

8. The assembly of claim 1, said individual radiation components comprising spatial resolution components derived from an image.

9. Apparatus comprising:
    an assembly operable to generate input radiation having a plurality of individual radiation components;
    a plurality of modulatable micro-mirrors located for receiving individual radiation components forming a part of said input radiation, said micro-mirrors being modulatable at different modulation rates in order to reflect individual radiation components therefrom at known and different modulation rates and with micro-mirror orientations for combining a number of the reflected individual radiation components to generate a combined reflection;
    a detector oriented to receive said combined reflection from said micro-mirrors, and operable to create an output signal representative of said combined number of individual radiation components; and
    an analyzer operably coupled with said detector to receive said output signal, and providing an individual analyses of at least some of said individual radiation components making up said combined reflection.

10. The assembly of claim 9, said analyzer comprising a computer operably coupled with said detector and micro-mirrors for controlling the modulation of said micro-mirrors and for providing said individual analyses.

11. The assembly of claim 9, further including a reflector positioned between the detector and the micro-mirrors and operable to receive said combined reflection from said micro-mirrors and to focus the combined reflection on said detector.

12. The assembly of claim 9, said analyzer operable to perform a mathematical manipulation upon said output.

13. The assembly of claim 9, said individual analyses comprising the energy magnitude of said individual radiation components.

14. The assembly of claim 9, said input radiation being infrared radiation.

15. The assembly of claim 9, said individual radiation components comprising different, substantially constant wavelength radiation components.

16. The assembly of claim 9, said individual radiation components comprising spatial resolution components derived from an image.

17. An analysis assembly for analyzing the absorption or attenuation by a sample of input radiation having a plurality of individual radiation components, said assembly comprising:

a plurality of modulatable devices located for receiving individual radiation components forming a part of said input radiation, said devices being modulatable at different modulation rates in order to project individual radiation components therefrom at known and different modulation rates for combining a number of the projected individual radiation components to generate a combined projection;

a detector oriented to receive said combined projection from said devices, and operable to create an output representative of said combined number of individual radiation components; and an analyzer operably coupled with said detector to receive said output, and providing an individual analyses of at least some of said individual radiation components making up said combined projection.

18. The analysis assembly of claim 17, wherein said assembly is operable for use as a variable filter.

* * * * *